US006200954B1

(12) United States Patent
Ge et al.

(10) Patent No.: US 6,200,954 B1
(45) Date of Patent: Mar. 13, 2001

(54) SMALL PEPTIDES HAVING POTENT ANTI-ANGIOGENIC ACTIVITY

(75) Inventors: Ruowen Ge; R. Manjunatha Kini, both of Singapore (SG)

(73) Assignee: National University of Singapore (SG)

( * ) Notice: Subject to any disclaimer, the term of this patent is extended or adjusted under 35 U.S.C. 154(b) by 0 days.

(21) Appl. No.: 09/385,442

(22) Filed: Aug. 30, 1999

Related U.S. Application Data

(60) Provisional application No. 60/099,313, filed on Sep. 4, 1998.

(51) Int. Cl.[7] .............................. A61K 38/00; A61K 38/17
(52) U.S. Cl. ................................ 514/12; 514/13; 514/14; 514/15; 514/16; 530/324; 530/325; 530/326; 530/327; 530/328; 530/329; 530/350; 536/235; 435/69.1; 435/240.2; 435/252.3; 435/254.11; 435/320.1
(58) Field of Search ..................................... 530/350, 324, 530/325, 326, 327, 328, 329; 514/12, 13, 14, 15, 16; 436/235; 435/69.1, 240.2, 252.3, 254.11, 320.1

(56) References Cited

U.S. PATENT DOCUMENTS

| 5,639,725 | 6/1997 | O'Reilly et al. ........................ 514/12 |
| 5,712,380 | * 1/1998 | Kendall .............................. 536/23.5 |

OTHER PUBLICATIONS

Wiesmann et al., Crystal Structure at 1.7 ↑ Resolution of VEGF in Complex with Domain 2 of the Flt–1 Receptor Cel. vol. 91, 695–704, Nov. 28, 1997.*
Judah Folkman et al, Cell, vol. 87, 1153–1156, Dec. 27, 1996.
Judah Folkman et al., Nature Medicine, vol. 1, No. 1, pp. 27–31 1999.
K. Jin Kim et al, Nature vol. 362, pp. 841–844, Apr. 29, 1993.
Judah Folkman, Cell. vol. 79, 315–328, Oct. 21, 1994.
Michael S. O'Reilly et al, Nature Medicine, vol. 2, No. 6, pp. 689–692 Jun. 1996.
Michael S. O'Reilly et al, Cell, vol. 88, 277–285, Jan. 24, 1997.
Thomas Boehm et al, Nature vol. 390 (27), pp. 404–407 Nov. 1997.
Robert S. Kerbel, Nature vol. 390 (27), pp. 335–336 Nov. 27, 1997.
Robert Handin et al, Heart Disease, A Textbook of Cardiovascular Medicine, Fourth Edition, pp. 1767–1789, 1992.
Birgit Millauer et al, Nature, vol. 367, pp. 576–579 Feb. 10, 1994.
Yihai Cao et al, The Journal of Biological Chemistry vol. 271, No. 46, pp. 29461–29467, 1996.
R. Manjunatha Kini et al, Current Topics in Peptide & Prot. Res. 1, pp. 297–311 (1994).

R. Manjunatha Kini et al, Biochemical and Biophysical, vol. 212, No. 3, 1995, Jun. 26, 1995, pp. 1115–1124.

Suk Paul Oh et al, Proc. Natl. Acad. Sci. USA, vol. 91, pp. 4229–4233, May 1994.

Marko Rehn et al, Proc. Natl. Acad. Sci. USA. vol. 91, pp. 4234–4238, May 1994.

Y. Muragaki et al, Proc. Natl., Acad. Sci, USA. vol. 92, pp. 8763–8767, Sep. 1995.

Yuan–Hua Ding et al., Proc. Natl., Acad. Sci. USA vol. 95, pp. 10443–10448, Sep. 1998.

Thomas Boehm et al, Biochemistry and Biophysical Research Comm. 252, pp. 190–194, (1998).

Napoleone Ferrara et al, Endocrine Reviews vol. 18, No. 1, pp. 4–24, 1997.

Bruce A. Keyt et al, The Journal of Biological Chemistry, vol. 271, No. 10, pp. 5638–5646, 1996.

Yves A. Muller et al. Proc. Natl. Acad. Sci. USA vol. 94, pp. 7192–7197, Jul. 1997.

Christian Wiesmann et al, Cell. vol. 91, 695–704 Nov. 28, 1997.

Bernhard Barleon et al, The Journal of Biological Chemistry, vol. 272, No. 16, pp. 10382–20388, 1997.

Sonia A. Cunningham, et al, Biochemistry and Biophysical Research Comm. vol. 231, pp. 596–599 (1997).

Hwai–Loonng Kong et al, Human Gene Therapy vol. 9, pp. 823–833 (Apr. 10, 1998).

Wanda Auerbach et al, Pharmac. Ther. vol. 63, pp. 265–311, 1994.

Yves A. Miller et al, Structure, vol. 5, pp. 1325–1338, Oct. 15, 1997.

* cited by examiner

*Primary Examiner*—F. T. Moezie
(74) *Attorney, Agent, or Firm*—Birch, Stewart, Kolasch & Birch LLP

(57) ABSTRACT

The present invention provides peptides having potent anti-angiogenic activity. The peptides can be administered as pharmaceutical compositions for prevention or treatment of undesired angiogenesis, for instance for prevention of tumor metastasis or inhibition of primary tumor growth.

12 Claims, 8 Drawing Sheets

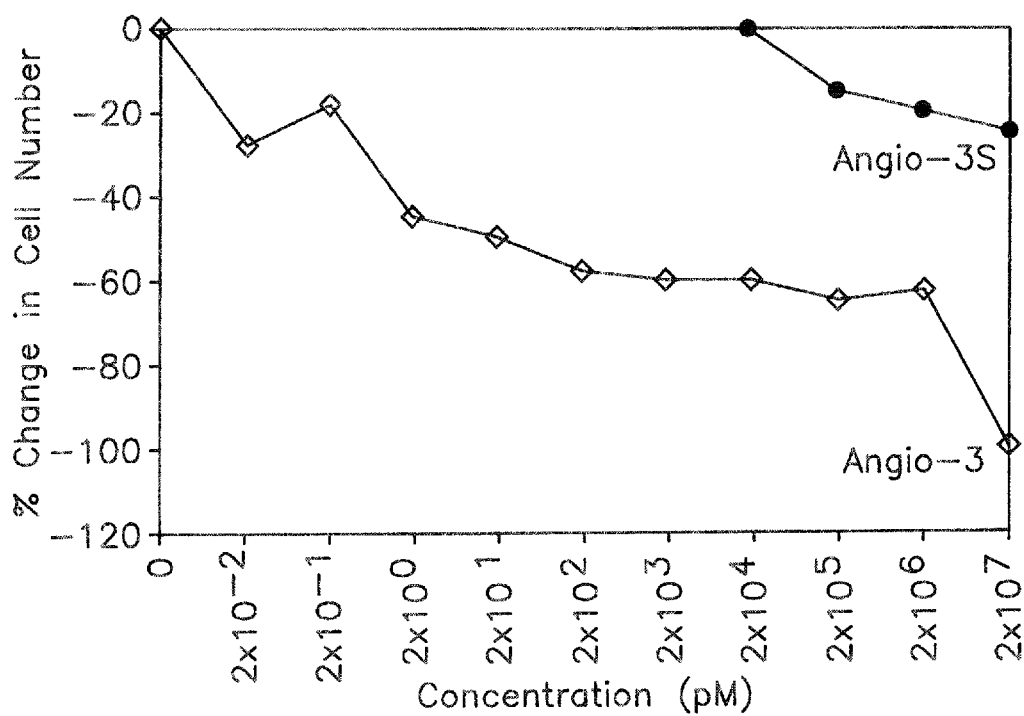
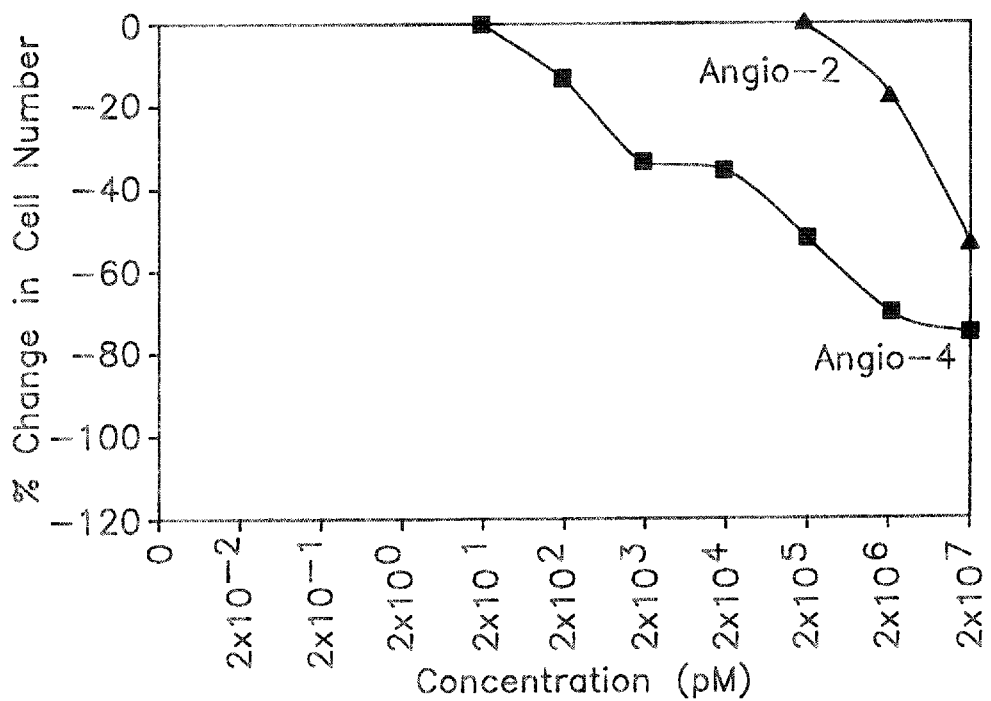

SMALL PEPTIDES HAVING POTENT ANTI-ANGIOGENIC ACTIVITY

This application claims priority on Provisional Application No. 60/099,313 filed on Sep. 4, 1998 now abandoned, the entire contents of which are hereby incorporated by reference.

FIELD OF THE INVENTION

The invention involves small peptides that function as potent angiogenic inhibitors. In particular, the invention relates to small peptides that can be synthesized by enzymatic or chemical methods. In addition, the invention relates to use of the small peptides to inhibit angiogenesis, to treat angiogenesis-related diseases and in angiogenesis research.

BACKGROUND OF THE INVENTION

Angiogenesis is the process of new blood vessel formation from pre-existing vessels. It plays important roles in many normal physiological functions such as embryonic development and wound healing (1). In addition, inappropriate angiogenesis is also associated with various pathological conditions including solid tumor growth and metastasis, rheumatoid arthritis and psoriasis (2). Many molecules that inhibit tumor angiogenesis have been shown to inhibit tumor growth including antibodies against angiogenic factors, natural and synthetic compounds that inhibit angiogenesis, and the natural angiogenic inhibitors like the angiostatin and endostatin proteins produced by tumor cells (3–8). Anti-cancer therapy by inhibiting tumor angiogenesis is called anti-angiogenic therapy and has shown great potential as an effective new method for treating cancer, especially solid tumors (9).

Plasminogen is a plasma glycoprotein synthesized mainly in the liver. It is the precursor of the serum protease plasmin that plays important roles in the fibrinolytic system and clot dissolution (10). At the amino terminus, plasminogen contains five homologous repeats that form looped "kringle" structures held together by disulfide bonds. Plasminogen binds to fibrin through lysine binding sites located on the five kringle domains (k1 through k5) (10). A naturally occurring fragment of plasminogen containing the first four kringle domains (k1–k4) has been isolated from serum and urine of mice bearing a low metastic Lewis lung carcinoma. This plasminogen fragment has been named angiostatin (equivalent to amino acids 98–440 of murine plasminogen) and is a potent angiogenesis inhibitor that can inhibit endothelial cell proliferation as well as tumor growth and metastasis in mice with no obvious toxicity (5, 6, 11). Furthermore, recombinant individual kringle domains of human plasminogen produced in *E. coli* have been found to be able to inhibit endothelial cell proliferation to various degrees with k5 the most potent, followed by k1 and k3 (12, 13). The k5 domain is not present in the naturally existing angiostatin protein.

Endostatin is a protein first identified from a hemangioendothelioma cell line in 1997 (17). It is a 20 kDa C-terminal fragment of collagen XVIII, a novel collagen that consists of a N-terminal region, a series of collagen-like domains with interruptions and a 35 kDa C-terminal noncollagenous domain (18, 19, 20). Recombinant endostatin functions as a potent angiogenesis inhibitor in vitro as well as in vivo (17). Systemic administration of endostatin to tumor bearing mice regressed the primary tumor without inducing drug resistance (21). Recently, endostatin was found to be a zinc-binding protein and the zinc-binding is essential for its antiangiogenic activity (22, 23). Human trials of endostatin are expected to be undertaken.

Vascular Endothelial Growth Factor (VEGF) is a potent endothelial specific mitogen. VEGF functions through two high affinity tyrosine kinase receptors: FLT-1 or Vascular Endothelial Growth Factor Receptor type 1 (FLT-1/VEGFR1) and FLK-1, also known as KDR or Vascular Endothelial Growth Factor Receptor type 2 (FLK-1/VEGFR2) and FLK-1/VEGFR2 (26). Both receptors are specifically expressed in endothelial cells. FLT-1 and KDR/FLK-1 stimulate endothelial cell proliferation and migration by binding to these two tyrosine kinase receptors (24). VEGF is also known as vascular permeability factor due to its ability to induce vascular leakage (24). The ligand binding domains of the two receptors as well as the receptor binding sites of VEGF have been studied by site-directed mutagenesis and X-ray crystallography (25, 26, 27, 28). VEGF binds its two receptors through different amino acid contacts (25). The first three immunoglobulin loops of the FLT-1 receptor seem to be the main area responsible for VEGF binding (29, 30). The signal transduction triggered by VEGF through its receptors play critical roles in both physiological angiogenesis as well as pathological angiogenesis such as solid tumor growth and metastasis by stimulating embryonic angiogenesis and tumor angiogenesis. An anti-VEGF monoclonal antibody has been shown to inhibit tumor growth in mice by reducing the vessel density of the tumor (14). Likewise, trans-dominant mutants of both receptors have been shown to inhibit tumor growth in mice (15).

It has also been observed that proline residues are sometimes found at the ends of the linear sequences that constitute the site of a protein-protein interaction (14, 15). However, the proline residues are not usually present within the interaction site.

SUMMARY OF THE INVENTION

The invention provides compositions comprising the peptides that are effective in inhibiting undesirable angiogenesis. The invention includes small peptides that have the ability to inhibit bovine aorta endothelial cell proliferation in the presence of basic Fibroblast Growth Factor (bFGF) in vitro. They can also inhibit angiogenesis in the chick chorioallantoic membrane (CAM) in vivo. The peptides of the invention are typically less than 20 amino acids in length. They preferably contain proline residues at each end or penultimate thereto. Peptides of the invention can be identified within the kringle domains of plasminogen or within the amino acid sequences of endostatin, VEGF, and VEGF receptors, especially FLT-1 and KDR/FLK-1.

Some preferred peptides of the invention are named Angio-1, Angio-2, Angio-3, Angio-4 and Angio-5 (SEQ. ID. NOs. 1–3, 11 and 12) according to the plasminogen kringle domains they are derived from. Other preferred peptides are shown in Table 1 (SEQ ID NOS. 29–50).

Methods for preventing or treating undesirable angiogenesis, for example to prevent tumor metastasis or inhibit the growth of a primary tumor, by administration of compositions of the anti-angiogenic peptides, are also within the scope of the invention.

BRIEF DESCRIPTION OF THE DRAWINGS

FIG. 1. Inhibition of BAE cell proliferation by peptide Angio 3.

FIG. 2. Inhibition of BAE cell proliferation by peptides Angio-2 and Angio-4.

FIG. 9A—0 hrs incubation; FIG. 9B—40 hours incubation.

FIG. 10. Antiangiogenic effect of peptides in the chick CAM assay. The number of positive inhibitions over the number of CAMs examined for each group are indicated above each bar.

FIG. 11. Antiangiogenic effect of peptides in the chick CAM assay. The number of positive inhibitions over the number of CAMs examined for each group are indicated above each bar.

DETAILED DESCRIPTION OF THE INVENTION

Figure 3:
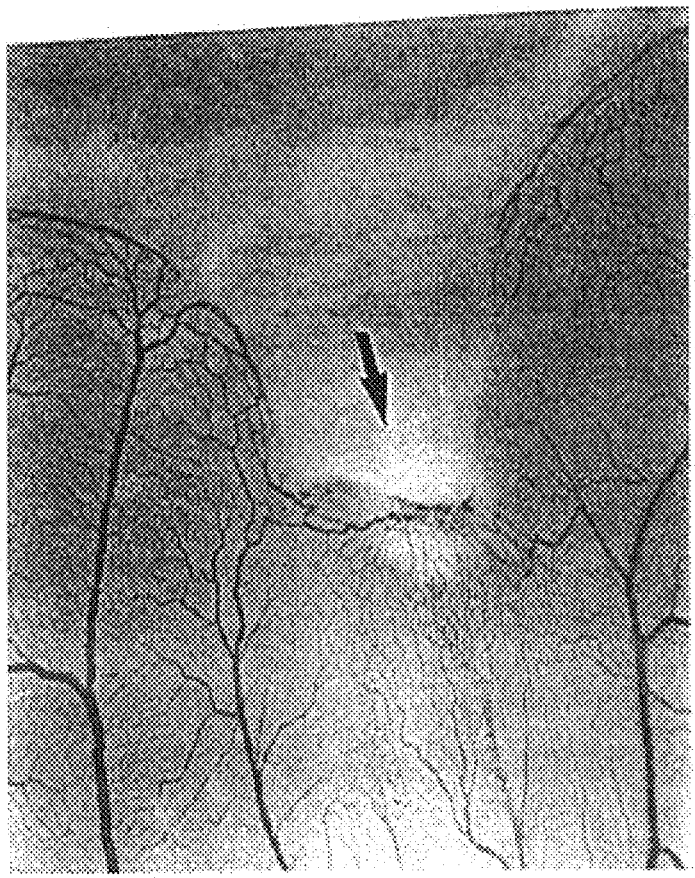
FIG. 3. Inhibition of chick CAM angiogenesis on 4 day embryo by Angio-3 at 120 ug/cover slip. The arrow indicates the inhibition of the growth of new vessels at the site of peptide application.

Small peptides were designed according to the amino acid sequences of the kringle domains of human plasminogen or from the amino acid sequences of endostatin, VEGF, FLT-1 or KDR/FLK-1 using the "proline bracket model" described in references 14 and 15. The peptides were synthesized using a peptide synthesizer (Applied Biosystems, Inc., model 473A). The peptides were then purified by typical HPLC methods using a C18 reverse-phase column and eluting with an acetonitrile gradient.

Angiostatin-derived peptides of the present invention represent a portion of a kringle domain of plasminogen. The effective portion of a kringle domain is generally residues 30 to 38 or 39 of a kringle domain, numbered as in reference 13. However, it is acceptable to add additional amino acids to this generally effective core peptide. Thus, peptides representing residues 27 to 40 or 41 of a kringle domain would be expected to be effective. Preferred peptides of the invention are derived from human or mouse plasminogen. The exemplified peptides of SEQ. ID. NOs.: 1–3, 11 and 12 represent residues 29–38 or 29–39 of human plasminogen kringle domains (13).

The peptides of the invention preferably range from 8 to 20 amino acids long. Peptides of the invention typically range from 7–20, more typically from 10–15 amino acids in length. The peptides are often about 10 amino acids in length. The peptides are more preferably 8, 9 or 10 residues long, most preferably 10 residues long.

The peptides of the invention may contain a single cysteine residue. In such a case, it is desirable that the cysteine residue be derivatized to block disulfide bond formation. Most preferably, peptides of the invention lack cysteine residues altogether.

The peptides also preferably contain a pair of proline residues. Each proline residue of the pair is preferably the residue penultimate to a terminus of a peptide, but either or both of the proline residues can be a terminal residue. Imino acids similar to proline, in that their side chains form a ring containing the peptide bonding nitrogen and $\alpha$-carbon, and that will "break" an $\alpha$-helix or $\beta$-sheet secondary structure, can be substituted for one or more of the proline residues. Exemplary peptides are shown as SEQ. ID. Nos. 1–50. The more preferred peptides are those of SEQ. ID. NOs. 1–3, 11, 12, 29–33, 35–38, 40–41 and 44–50.

The peptides of the invention are active in inhibiting angiogenesis in the in vitro bovine aorta endothelial (BAE) cell proliferation assay with an $IC_{50}$ of 20 $\mu$M or less, preferably 5 $\mu$M or less, more preferably 1 $\mu$M or less and most preferably below 0.1 $\mu$M. Much preferred peptides of the invention are active in the in vitro BAE cell proliferation assay with an $IC_{50}$ of about 20 pM.

Alternatively, preferred peptides of the invention will exhibit inhibition of angiogenesis in a chick chorioallantoic membrane assay of at least 30% (i.e. inhibition is observed under at least 3 of 10 coverslips applied) at a dose of 50 $\mu$g/coverslip. More preferably at least 50% inhibition is observed at a dose of 25 $\mu$g/coverslip. Most preferably, inhibition in the range of 50–80% is observed for a dose ranging from 10–25 $\mu$g/coverslip.

Also, the peptides of the invention encompass peptides that have been derivatized, for example to improve transport across membranes by attachment of hydrophobic groups or that are carboxy-terminal amidated to improve resistance to serum proteases. Methods for accomplishing such derivatizations are known in the art.

Formulation of the peptides for administration is standard in the art. It is anticipated that optimization of formulation, dosages and schedule of administration is also standard in the art. Reference 16, especially at parts 4, 5 and 7, provides guidance in these matters. Administration of the peptides for anti-tumor treatment can be by any route, preferably oral, intravenous, intradermal, subcutaneous or aerosol. It is expected that subcutaneous administration is especially effective when anti-metastatic activity is desired (see, reference 6).

The dosage of the peptides will depend upon the therapeutic index of the compound. It is noted that angiostatin has been administered to mice in amounts of 100 mg/kg/day without observable toxicity. Inhibition of metastasis by angiostatin is observed at doses of about 1 mg/kg/day and inhibition of primary tumor growth is observed at about 10 mg/kg/day (6). Thus, it is expected that effective doses of the peptides of the present invention will be about 0.2 $\mu$g/kg/day to about 2 mg/kg/day for inhibition of metastasis. Preferred dosages are in the 2–200 $\mu$g/kg/day range, most preferred dosages are in the 20–50 $\mu$g/kg/day range. It is expected that the dosage ranges will be about 10-fold higher for inhibition of primary tumor growth.

EXAMPLE 1

Anti-proliferative Activity of Peptides Derived from Angiostatin

The peptides were tested in an in vitro bovine aorta endothelial cell (BAE) proliferation assay for their ability to inhibit BAE cell proliferation. Cells were plated into 24-well culture plates at $1.25 \times 10^4$ cells/well in complete SFM-endothelial medium (Gibco, USA). After 24 h, the medium was removed and various amounts of peptides were added into the wells in 0.5 ml of SFM-endothelial medium without bFGF. After 30 minutes incubation, bFGF was added into each well at a final concentration of 1 ng/ml together with another 0.5 ml of SFM-endothelial medium. Seventy-two hours later, cells were trypsinized and counted using a hemocytometer. Commercial *E. coli* recombinant human angiostatin (1 µM) was used as a control in the experiments. Peptides Angio-2, Angio-3 and Angio-4, containing sequences from kringles 2, 3 and 4 of human plasminogen (SEQ. ID. Nos. 2, 3 and 11), all inhibited BAE cell proliferation in a dose-dependent manner (FIGS. 2 and 3). The $IC_{50}$ of the three peptides are about 20 uM, 20 pm and 2 uM respectively. It is noted that peptide Angio-3 inhibited BAE cell proliferation with an $IC_{50}$ in a range much lower than the reported nanomolar range of angiostatin protein (5). In contrast, a randomly scrambled version of Angio-3 (Angio-3S) in which the same amino acids present in Angio-3 were put in a random order, completely lost angiogenesis inhibition ability (FIG. 2). The BAE inhibition assay provides a method for determining the anti-angiogenic activity of peptides. For example, peptides Angio-3A, -3B, -3C, -3D, -3E and -3F (SEQ. ID. Nos. 4–9) are peptides in which the six amino acids surrounded by the two prolines are individually mutated into alanine. The contribution of each of the six amino acids between the proline residues to the biological activity of Angio-3 can be determined by testing these peptides.

EXAMPLE 2

Anti-angiogenic Activity of Peptides Derived from Angiostatin

Figure 4:
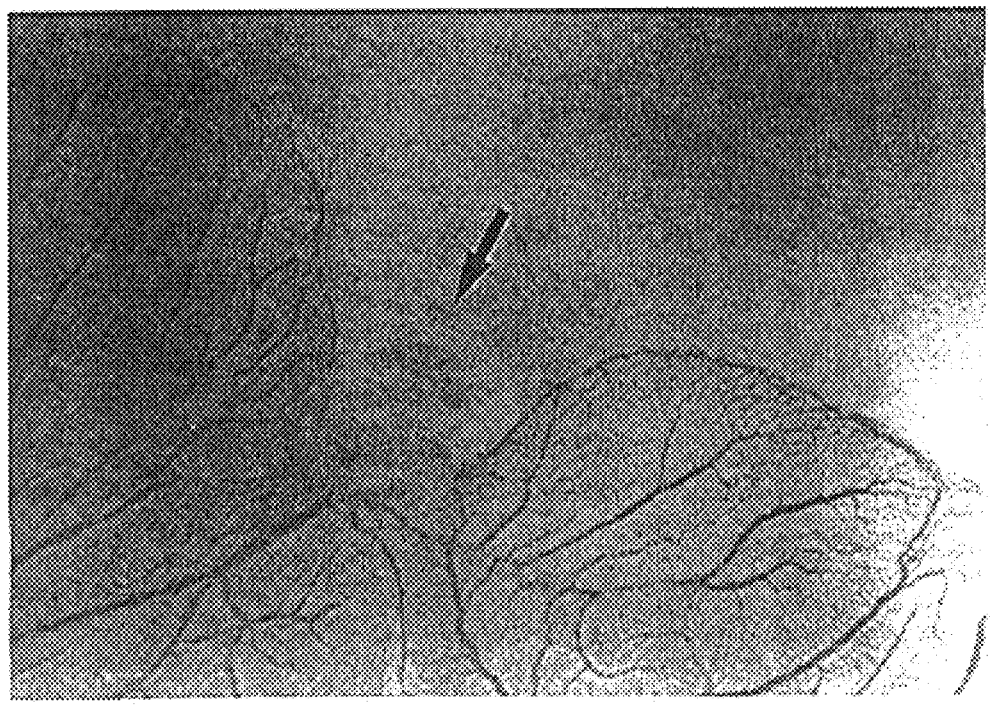
FIG. 4. Inhibition of chick CAM angiogenesis on 4 day embryo by Angio-4 at 120 ug/cover slip. Arrows indicate the inhibition of the growth of new vessels at the site of peptide application.
Figure 5:
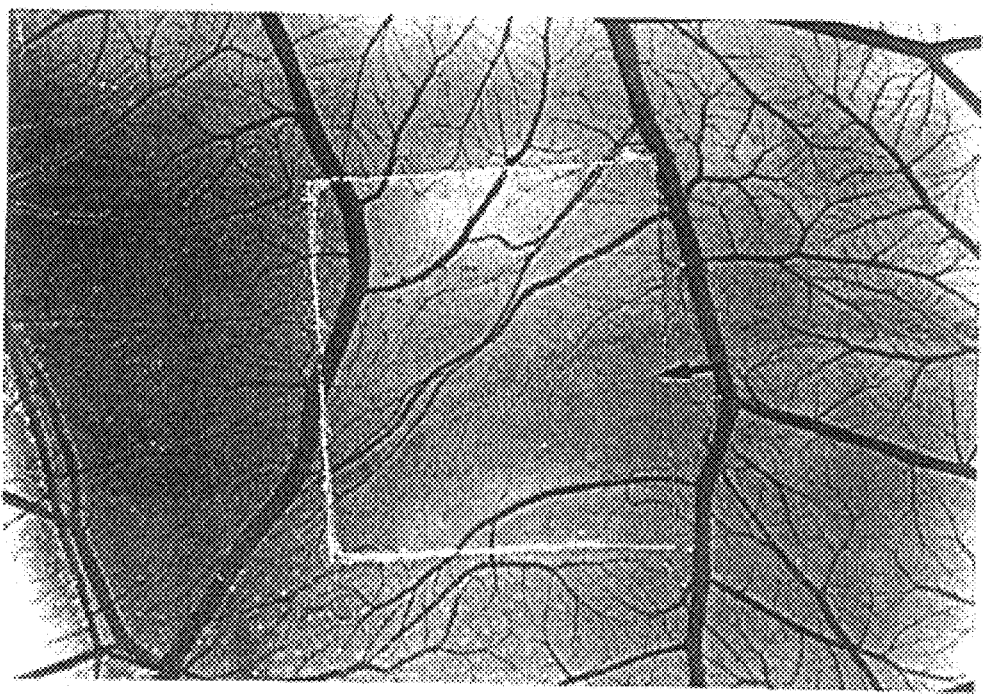
FIG. 5. Inhibition of chick CAM angiogenesis on 10 day embryo by Angio-2 at 12 ug/cover slip.
Figure 6:
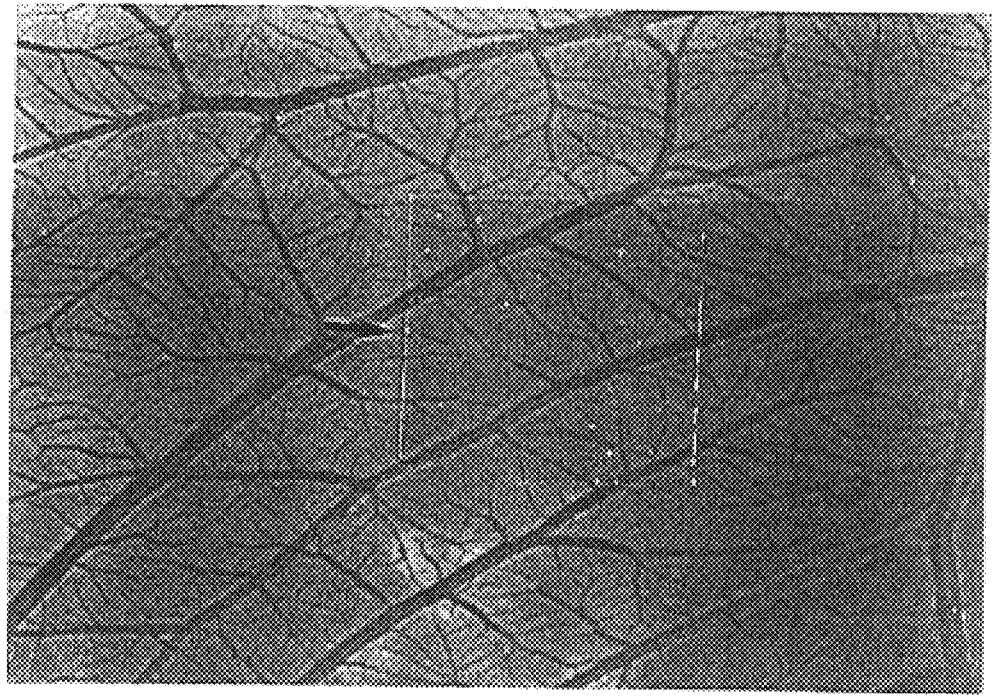
FIG. 6. Control cover slip containing PBS on 10 day old chick embryo CAM. The arrow indicates the position of the control cover slip on CAM.

Since peptides Angio-2, Angio-3 and Angio-4 all inhibited BAE cell proliferation, they were also tested in the chick embryo chorioallantoic membrane (CAM) in vivo angiogenesis assay (7). In this assay, the peptides are coated onto 2–3 mm glass squares cut from microscope cover slips. All three peptides inhibited chick CAM angiogenesis (FIGS. 4, 5 and 6). Peptide Angio-3 reduced microvessel density at the very low dose of 12 pg/cover slip (the lowest dose tested, comparing to a PBS control). As a positive control, recombinant angiostatin at the dose of 100 ug/cover slip was tested in the same experiment. The amount of inhibition (judging from the extent of reduction in microvessel density) from 100 ug recombinant angiostatin is equivalent to 1.2 ug of Angio-3 peptide. Based on this, we estimated that Angio-3 is at least as potent as angiostatin in inhibiting chick CAM angiogenesis.

At high doses, e.g., 1 mg/cover slip, the blood vessels under the cover slip containing all three peptides died and circulation was stopped. The color of the blood changed into dark red instead of the bright red of the circulating blood.

The above data demonstrated that Angio-2, Angio-3 and Angio-4, small peptides derived from the sequence of human plasminogen kringle domains 2, 3 and 4 function as potent angiogenesis inhibitors. Importantly, peptide Angio-3 is more potent in inhibiting BAE cell proliferation compared to angiostatin protein and at least as potent as recombinant angiostatin in inhibiting chick CAM angiogenesis.

Cao et al. (12) show that integrity of complete kringle domains is required for anti-angiogenic activity of angiostatin and that a tandem pair of properly folded domains is necessary. Cao et al. (13) also show that, at least with respect to the k5 domain, appropriate disulfide bond formation is necessary for maintaining anti-angiogenic activity. Thus, it is surprising that the exemplified small peptides of the invention, which (1) do not form complete kringle domains and (2) do not contain any cysteine residues and therefore do not form disulfide bonds, have such high activity.

EXAMPLE 3

Figure 7:
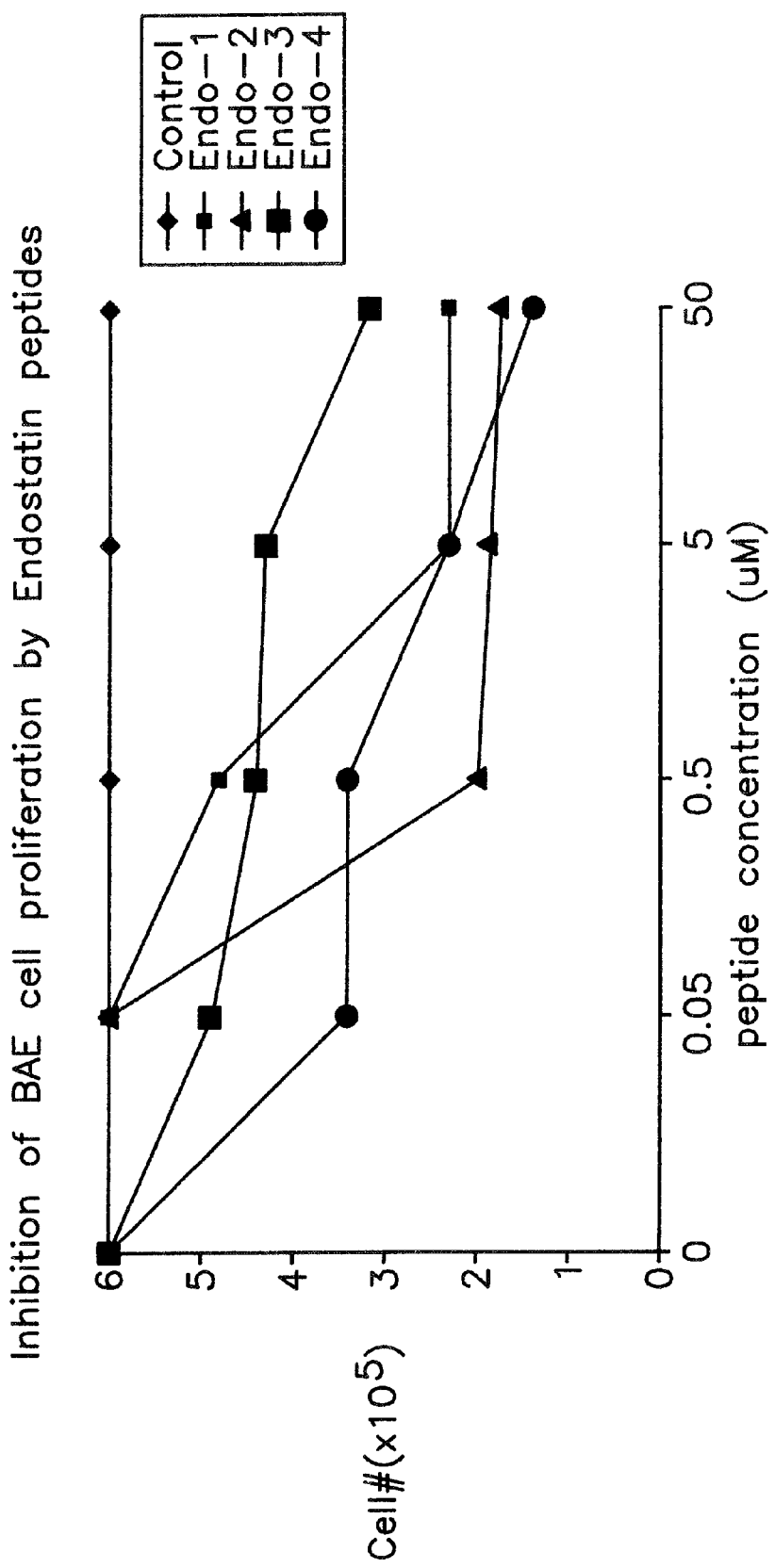
FIG. 7. Inhibition of BAE cell proliferation by peptides Endo-1, Endo-2, Endo-3 and Endo-4.

Antiangiogenic Activity of Peptides Derived from Endostatin, VEGF and VEGF Receptors Peptides were tested in an in vitro bovine aorta endothelial cell (BAE) proliferation assay for their ability to inhibit BAE cell proliferation. Cells were plated into 24-well culture plates at the number of $1.25 \times 10^4$/ well in complete SFM-endothelial media (Gibco, USA). After 24 hours, the medium was removed and various amounts of peptides were added into the wells in 0.5 ml of SFM-endothelial medium without bFGF. After 30 minutes incubation, bFGF was added into each well at a final concentration of 1 ng/ml together with another 0.5 ml of SFM-endothelial medium. Seventy-two hours later, cells were trypsinized and counted using a hemocytometer. Peptides Endo-2, Endo-3 and Endo-4 all inhibited BAE cell proliferation in a dose-dependent manner while peptide Endo-1 has only a slight inhibition effect at high doses (FIG. 7). The $IC_{50}$ of the Endo-2, -3 and -4 peptides is estimated to be 0.4 uM, 0.3 uM and 2 uM respectively.

Figure 8:
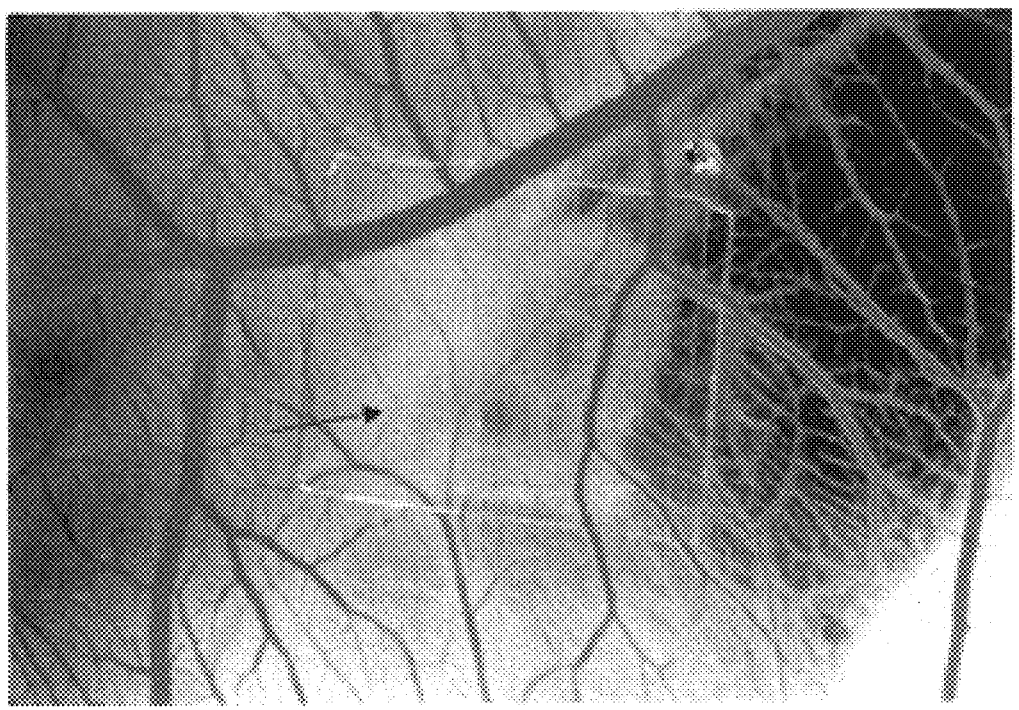
FIG. 8. Inhibition of chick -CAM angiogenesis in 10 day embryo by Endo-4 at 1.8 $\mu$g/coverslip.

All 4 endostatin-derived peptides were also tested in the chick embryo chorioallantoic membrane (CAM) in vivo angiogenesis assay. These peptides reduced microvessel density with various efficacy comparing to a PBS control (FIG. 8).

Figure 9A:
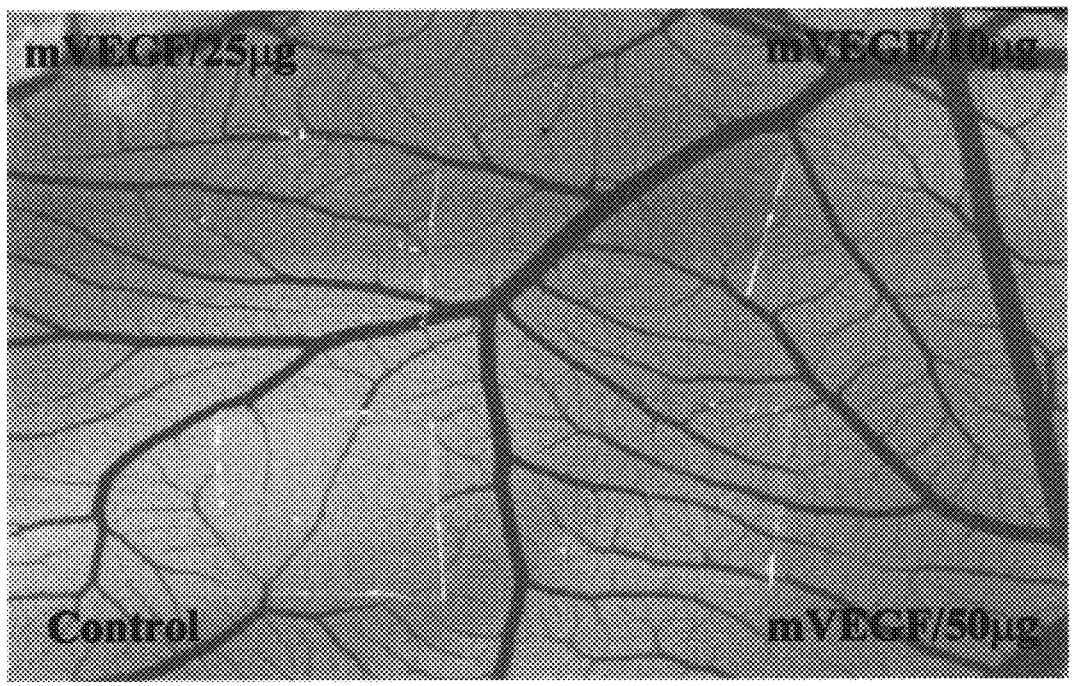
FIGS. 9A–9B. Inhibition of chick CAM angiogenesis in 13 day embryo by mVEGF peptide at various doses as indicated. Arrows indicate the inhibition of growth of new vessels at the site of peptide application.
Figure 9B:
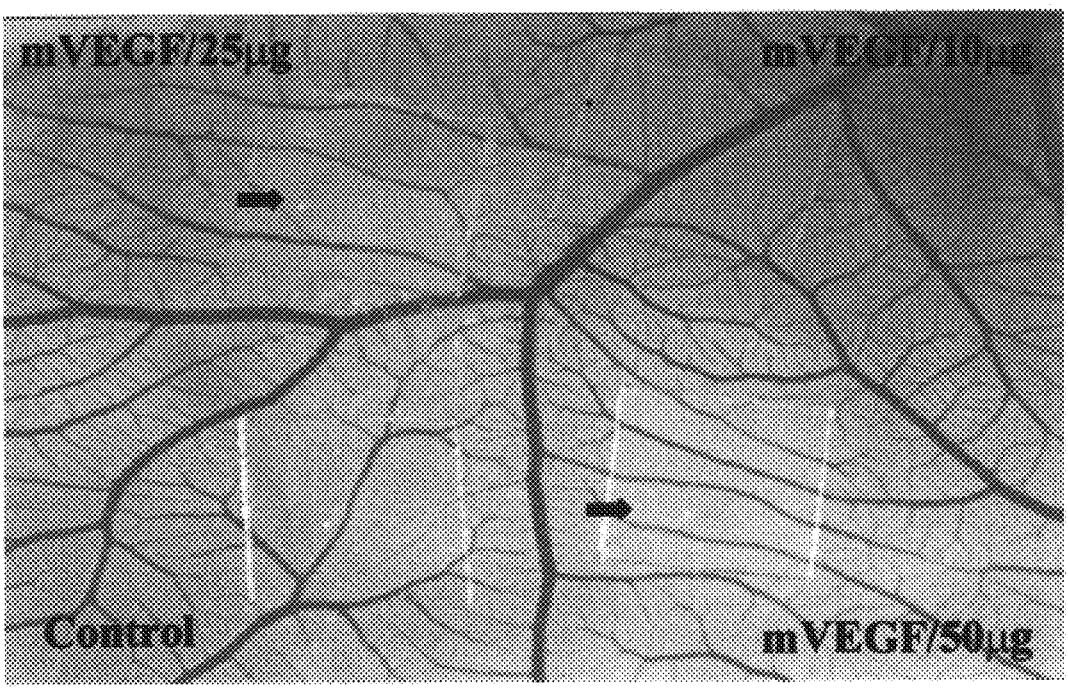
Figure 10:
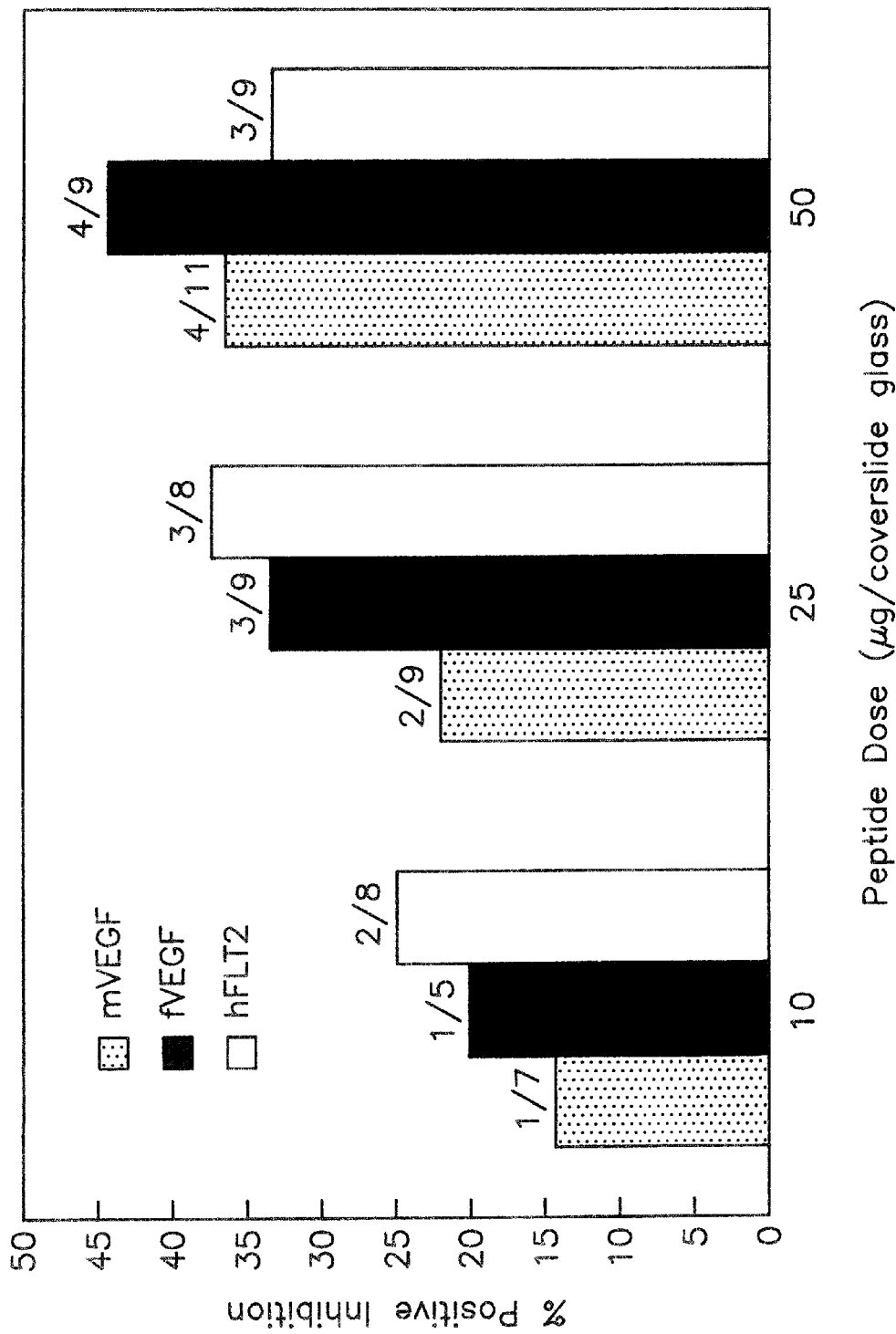

Peptides designed from mammalian VEGF sequences (mVEGF) and Zebrafish VEGF (fVEGF) showed dose-dependent inhibition of CAM angiogenesis (FIGS. 9,10). Scrambled mutant peptide where the same amino acids in mVEGF were placed in a random order completely destroyed the angiogenesis inhibition activity of mVEGF peptide.

Figure 11:
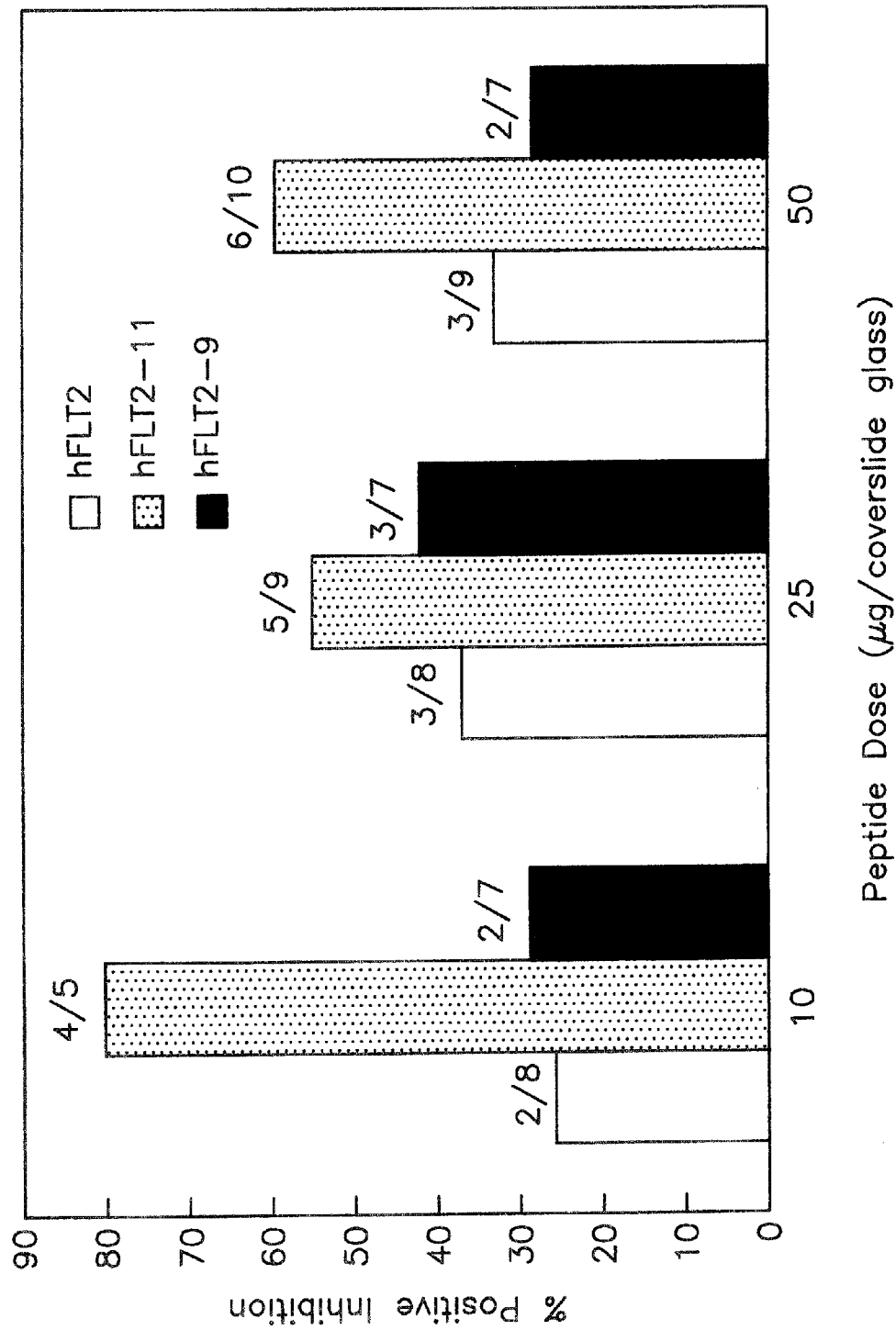

Two small peptides, hFLT1 and hFLT2, were designed from the second immunoglobulin domain (Ig domain 2) of the extracellular region of FLT-1. The peptide hFLT2 showed very potent angiogenesis inhibition activity on CAM (FIGS. 10 and 11). Surprisingly, a truncated version of hFLT2 peptide, hFLT2–11, in which the N-terminal two amino acids have been deleted, showed a even more potent antiangiogenic activity comparing to hFLT2 (FIG. 11). However, a single amino acid mutated version of the same peptide, hFLT2-T, in which the second amino acid proline was replaced with threonine, has a much weaker antiangiogenic activity (FIG. 11). Peptide hFLT2–9 in which four amino acids were removed from the N-terminal of hFLT2, showed similar level of antiangiogenic activity as the original peptide (FIG. 11). Further truncation at the N-terminal of the peptide resulted in non-functional peptide (hFLT2–7 and hFLT2–5).

The above data demonstrated that small peptides derived from the sequence of human endostatin, VEGF and FLT-1 can function as potent angiogenesis inhibitors.
SEQUENCE LISTING A Sequence Listing presenting SEQ. ID. NOs. 1–50 is appended hereto as part of the present application.
REFERENCES:

The following articles of the periodical and patent literature are cited above. Each is hereby incorporated in its entirety by reference by such citation.

1. Folkman, J. et al., *Cell* 87, 1153–1155, 1996 and U.S. Pat. No. 5,639,735.

2. Folkman, J. et al., *J. Nature Medicine* 1, 27–31, 1995.
3. Kim, K. J. et al., *Nature* 362, 841–844, 1993.
4. Auerbach, W. et al., *Pharmac. Ther.* 63, 265–311, 1994.
5. O'Reilly, M. S. et al., *Cell* 79, 315–328, 1994.
6. O'Reilly, M. S. et al., *Nature Medicine* 2, 689–692, 1996.
7. O'Reilly, M. S. et al., *Cell* 88, 277–285, 1997.
8. Boehm, T. et al., *Nature* 390, 404–407, 1997.
9. Kerbel, R. S., *Nature* 390, 335–336, 1997.
10. Handin, R. I. et al., Chapter 58 of "Heart Diseases: A Textbook Of Cardiovascular Medicine," 4th ed. c. 1992 by W. B. Saunders Company, pp. 1767–1789.
11. O'Reilly, M. S. et al. U.S. Pat. No. 5,639,725, 1997.
12. Cao, Y. et al., *J. Biol. Chem.* 271, 29461–29467, 1996.
13. Cao, Y. et al., *J. Biol. Chem.* 272, 22924–22928, 1997.
14. Kini, R. M. et al., *Curr. Topic Peptides & Prot. Res.* 1, 297–311, 1994.
15. Kini, R. M. et al., *Biochem. Biophy. Res. Comm.* 212, 1115–1124, 1995.
16. "Remington: The Science and Practice of Pharmacy", 19th ed., c. 1995 by the Philadelphia College of Pharmacy and Science.
17. Oh, S. P. et al., *PNAS USA* 91, 4229–4233, 1994.
18. Rehn, M. et al., *PNAS USA* 91, 4234–4238, 1994.
19. Muragaki, Y. et al., *PNAS USA* 92, 8763–8767, 1995.
20. Ding, Y-H et al., *PNAS USA* 95, 10443–10448, 1998.
21. Boehm, T. et al., *Biochem. Biophy. Res. Comm.* 252, 190–194, 1998.
22. Ferrara, N. et al., *Endo. Rev.* 18, 4–25, 1997.
23. Keyt, B. A. et al., *J. Biol. Chem.* 271, 5638–5646, 1996.
24. Muller, Y. A. et al., *PNAS USA* 94, 7194–7197, 1997.
25. Muller, Y. A. et al., *Structure* 5, 1325–1338, 1997.
26. Weismann, C. et al., *Cell* 91, 695–704, 1997.
27. Barleon, B. et al,. *J. Biol. Chem.* 272, 10382–10388, 1997.
28. Cunningham, S. A. et al., *Biochem. Biophy. Res. Comm.* 231, 569–599, 1997.
29. Millauer, B. et al., *Nature* 367, 576–579, 1994.
30. Kong, H. et al., *Human Gene Therapy* 9, 823–833, 1998.

What is claimed is:

1. A peptide comprising a portion of a FLT-1 protein, wherein said peptide is of length from 7–20 amino acids long and wherein said peptide exhibits an $IC_{50}$ of 20 μM or less in a bovine aorta endothelial cell proliferation assay or exhibits inhibition of angiogenesis in a chick chorioallantoic membrane assay of at least 30% at a dose of 50 μg/coverslip.

2. The peptide of claim 1 that exhibits an $IC_{50}$ of 20 pM to 1 μM in a bovine aorta endothelial cell assay or exhibits inhibition of angiogenesis in a chick chorioallantoic membrane assay of at least 50% at a dose of 10 to 25 μg/coverslip.

3. The peptide of claim 1 that has a length of from 9 to 20 amino acids long.

4. The peptide of claim 1, comprising a peptide having an amino acid sequence selected from the group consisting of SEQ. ID. NOs. 37 and 40–41.

5. A pharmaceutical composition comprising a peptide according to claim 1 and a pharmaceutically acceptable carrier.

6. The composition according to claim 5, wherein said composition provides a unit dose of from 20 μg/kg/day to 2 mg/kg/day.

7. The peptide of claim 1, comprising a peptide having an amino acid sequence selected from the group consisting of SEQ ID NOS:36–46.

8. A pharmaceutical composition comprising at least one peptide according to claim 4 and a pharmaceutically acceptable carrier.

9. A pharmaceutical composition comprising at least one peptide according to claim 7 and a pharmaceutically acceptable carrier.

10. The composition according to claim 9, wherein said composition provides a unit dose of from 20 μg/kg/day to 2 mg/kg/day.

11. The peptide of claim 1 that lacks any cysteine or if it contains any cysteine, the cysteine is blocked to prevent disulfide formation.

12. The peptide of claim 3 that lacks any cysteine or if it contains any cysteine, the cysteine is blocked to prevent disulfide formation.

* * * * *

SEQUENCE LISTING

```
<160> NUMBER OF SEQ ID NOS: 50

<210> SEQ ID NO 1
<211> LENGTH: 10
<212> TYPE: PRT
<213> ORGANISM: mammalian
<220> FEATURE:
<223> OTHER INFORMATION: Angio-1

<400> SEQUENCE: 1

Ser Pro His Arg Pro Arg Phe Ser Pro Ala
 1               5                   10

<210> SEQ ID NO 2
<211> LENGTH: 10
<212> TYPE: PRT
<213> ORGANISM: mammalian
<220> FEATURE:
<223> OTHER INFORMATION: Angio-2

<400> SEQUENCE: 2

Ser Pro His Ala His Gly Tyr Ile Pro Ser
 1               5                   10

<210> SEQ ID NO 3
<211> LENGTH: 10
<212> TYPE: PRT
<213> ORGANISM: mammalian
<220> FEATURE:
<223> OTHER INFORMATION: Angio-3

<400> SEQUENCE: 3

Thr Pro His Thr His Asn Arg Thr Pro Glu
 1               5                   10

<210> SEQ ID NO 4
<211> LENGTH: 10
<212> TYPE: PRT
<213> ORGANISM: mammalian

<400> SEQUENCE: 4
```

```
Thr Pro Ala Thr His Asn Arg Thr Pro Glu
 1               5                  10
```

<210> SEQ ID NO 5
<211> LENGTH: 10
<212> TYPE: PRT
<213> ORGANISM: mammalian

<400> SEQUENCE: 5

```
Thr Pro His Ala His Asn Arg Thr Pro Glu
 1               5                  10
```

<210> SEQ ID NO 6
<211> LENGTH: 10
<212> TYPE: PRT
<213> ORGANISM: mammalian

<400> SEQUENCE: 6

```
Thr Pro His Thr Ala Asn Arg Thr Pro Glu
 1               5                  10
```

<210> SEQ ID NO 7
<211> LENGTH: 10
<212> TYPE: PRT
<213> ORGANISM: mammalian

<400> SEQUENCE: 7

```
Thr Pro His Thr His Ala Arg Thr Pro Glu
 1               5                  10
```

<210> SEQ ID NO 8
<211> LENGTH: 10
<212> TYPE: PRT
<213> ORGANISM: mammalian

<400> SEQUENCE: 8

```
Thr Pro His Thr His Asn Ala Thr Pro Glu
 1               5                  10
```

<210> SEQ ID NO 9
<211> LENGTH: 10
<212> TYPE: PRT
<213> ORGANISM: mammalian

<400> SEQUENCE: 9

```
Thr Pro His Thr His Asn Arg Ala Pro Glu
 1               5                  10
```

<210> SEQ ID NO 10
<211> LENGTH: 10
<212> TYPE: PRT
<213> ORGANISM: mammalian

<400> SEQUENCE: 10

```
Asn Thr Thr Glu Thr Pro His Pro His Arg
 1               5                  10
```

<210> SEQ ID NO 11
<211> LENGTH: 10
<212> TYPE: PRT
<213> ORGANISM: mammalian
<220> FEATURE:
<223> OTHER INFORMATION: Angio-4

<400> SEQUENCE: 11

Thr Pro His Arg His Gln Lys Thr Pro Glu
 1               5                  10

<210> SEQ ID NO 12
<211> LENGTH: 11
<212> TYPE: PRT
<213> ORGANISM: mammalian
<220> FEATURE:
<223> OTHER INFORMATION: Angio-5

<400> SEQUENCE: 12

Glu Pro His Arg His Ser Ile Phe Thr Pro Glu
 1               5                  10

<210> SEQ ID NO 13
<211> LENGTH: 10
<212> TYPE: PRT
<213> ORGANISM: mammalian

<400> SEQUENCE: 13

Thr Pro His Arg His Asn Arg Thr Pro Glu
 1               5                  10

<210> SEQ ID NO 14
<211> LENGTH: 10
<212> TYPE: PRT
<213> ORGANISM: mammalian

<400> SEQUENCE: 14

Thr Pro His Lys His Asn Arg Thr Pro Glu
 1               5                  10

<210> SEQ ID NO 15
<211> LENGTH: 10
<212> TYPE: PRT
<213> ORGANISM: mammalian

<400> SEQUENCE: 15

Ser Pro His Lys His Asn Arg Thr Pro Glu
 1               5                  10

<210> SEQ ID NO 16
<211> LENGTH: 10
<212> TYPE: PRT
<213> ORGANISM: mammalian

<400> SEQUENCE: 16

Phe Pro His Val Pro Asn Tyr Ser Pro Ser
 1               5                  10

<210> SEQ ID NO 17
<211> LENGTH: 10
<212> TYPE: PRT
<213> ORGANISM: mammalian

<400> SEQUENCE: 17

Ser Pro His Arg Pro Thr Phe Ser Pro Ala
 1               5                  10

<210> SEQ ID NO 18
<211> LENGTH: 10
<212> TYPE: PRT
<213> ORGANISM: mammalian

<400> SEQUENCE: 18

-continued

```
Ser Pro His Ile Pro Lys Tyr Ser Pro Glu
 1               5                  10
```

<210> SEQ ID NO 19
<211> LENGTH: 10
<212> TYPE: PRT
<213> ORGANISM: mammalian

<400> SEQUENCE: 19

```
Ser Pro His Val Pro Lys Phe Ser Pro Glu
 1               5                  10
```

<210> SEQ ID NO 20
<211> LENGTH: 10
<212> TYPE: PRT
<213> ORGANISM: mammalian

<400> SEQUENCE: 20

```
Ser Pro His Ala His Gly Tyr Ile Pro Ala
 1               5                  10
```

<210> SEQ ID NO 21
<211> LENGTH: 10
<212> TYPE: PRT
<213> ORGANISM: mammalian

<400> SEQUENCE: 21

```
Ser Pro His Ala His Gly Tyr Leu Pro Ser
 1               5                  10
```

<210> SEQ ID NO 22
<211> LENGTH: 10
<212> TYPE: PRT
<213> ORGANISM: mammalian

<400> SEQUENCE: 22

```
Phe Pro His Arg His Ser Lys Thr Pro Glu
 1               5                  10
```

<210> SEQ ID NO 23
<211> LENGTH: 10
<212> TYPE: PRT
<213> ORGANISM: mammalian

<400> SEQUENCE: 23

```
Thr Pro His Trp His Glu Lys Thr Pro Glu
 1               5                  10
```

<210> SEQ ID NO 24
<211> LENGTH: 10
<212> TYPE: PRT
<213> ORGANISM: mammalian

<400> SEQUENCE: 24

```
Thr Pro His Arg His Glu Lys Thr Pro Gly
 1               5                  10
```

<210> SEQ ID NO 25
<211> LENGTH: 10
<212> TYPE: PRT
<213> ORGANISM: mammalian

<400> SEQUENCE: 25

```
Thr Pro His Arg His Leu Lys Thr Pro Glu
 1               5                  10
```

<210> SEQ ID NO 26
<211> LENGTH: 11
<212> TYPE: PRT
<213> ORGANISM: mammalian

<400> SEQUENCE: 26

Glu Pro His Arg His Ser Ile Phe Thr Pro Gln
 1               5                  10

<210> SEQ ID NO 27
<211> LENGTH: 11
<212> TYPE: PRT
<213> ORGANISM: mammalian

<400> SEQUENCE: 27

Glu Pro His Ser His Arg Ile Phe Thr Pro Glu
 1               5                  10

<210> SEQ ID NO 28
<211> LENGTH: 11
<212> TYPE: PRT
<213> ORGANISM: mammalian

<400> SEQUENCE: 28

Glu Pro His Gln His Ser Ile Phe Thr Pro Glu
 1               5                  10

<210> SEQ ID NO 29
<211> LENGTH: 11
<212> TYPE: PRT
<213> ORGANISM: mammalian
<220> FEATURE:
<223> OTHER INFORMATION: Endo-1

<400> SEQUENCE: 29

Ser Pro His Asn Ser Tyr Ile Val Leu Pro Ile
 1               5                  10

<210> SEQ ID NO 30
<211> LENGTH: 13
<212> TYPE: PRT
<213> ORGANISM: mammalian
<220> FEATURE:
<223> OTHER INFORMATION: Endo-2

<400> SEQUENCE: 30

Gln Pro Val Leu His Leu Val Ala Leu Asn Thr Pro Leu
 1               5                  10

<210> SEQ ID NO 31
<211> LENGTH: 14
<212> TYPE: PRT
<213> ORGANISM: mammalian
<220> FEATURE:
<223> OTHER INFORMATION: Endo-3

<400> SEQUENCE: 31

Val Pro Ile Val Asn Leu Lys Asp Glu Val Leu Ser Pro Ser
 1               5                  10

<210> SEQ ID NO 32
<211> LENGTH: 16
<212> TYPE: PRT
<213> ORGANISM: mammalian
<220> FEATURE:

```
<223> OTHER INFORMATION: Endo-4

<400> SEQUENCE: 32

His Pro Ala Trp Pro Gln Lys Ser Val Trp His Gly Ser Asp Pro Ser
 1               5                  10                  15

<210> SEQ ID NO 33
<211> LENGTH: 12
<212> TYPE: PRT
<213> ORGANISM: mammalian
<220> FEATURE:
<223> OTHER INFORMATION: mVEGF

<400> SEQUENCE: 33

Tyr Pro Asp Glu Ile Glu Tyr Ile Phe Lys Pro Ser
 1               5                  10

<210> SEQ ID NO 34
<211> LENGTH: 12
<212> TYPE: PRT
<213> ORGANISM: mammalian
<220> FEATURE:
<223> OTHER INFORMATION: smVEGF

<400> SEQUENCE: 34

Tyr Ile Glu Glu Tyr Ser Pro Asp Ile Pro Phe Lys
 1               5                  10

<210> SEQ ID NO 35
<211> LENGTH: 12
<212> TYPE: PRT
<213> ORGANISM: mammalian
<220> FEATURE:
<223> OTHER INFORMATION: fVEGF

<400> SEQUENCE: 35

Tyr Pro Asp Glu Ile Glu His Thr Tyr Ile Pro Ser
 1               5                  10

<210> SEQ ID NO 36
<211> LENGTH: 12
<212> TYPE: PRT
<213> ORGANISM: mammalian
<220> FEATURE:
<223> OTHER INFORMATION: hFLT1

<400> SEQUENCE: 36

Arg Pro Phe Val Glu Met Tyr Ser Glu Ile Pro Glu
 1               5                  10

<210> SEQ ID NO 37
<211> LENGTH: 13
<212> TYPE: PRT
<213> ORGANISM: mammalian
<220> FEATURE:
<223> OTHER INFORMATION: hFLT-2T

<400> SEQUENCE: 37

Ser Thr Asn Ile Thr Val Thr Leu Lys Lys Phe Pro Leu
 1               5                  10

<210> SEQ ID NO 38
<211> LENGTH: 13
<212> TYPE: PRT
<213> ORGANISM: mammalian
<220> FEATURE:
<223> OTHER INFORMATION: hFLT2
```

<400> SEQUENCE: 38

Ser Pro Asn Ile Thr Val Thr Leu Lys Lys Phe Pro Leu
1               5                   10

<210> SEQ ID NO 39
<211> LENGTH: 13
<212> TYPE: PRT
<213> ORGANISM: mammalian
<220> FEATURE:
<223> OTHER INFORMATION: shFLT2

<400> SEQUENCE: 39

Leu Val Pro Leu Pro Lys Ile Lys Asn Ser Thr Phe Thr
1               5                   10

<210> SEQ ID NO 40
<211> LENGTH: 11
<212> TYPE: PRT
<213> ORGANISM: mammalian
<220> FEATURE:
<223> OTHER INFORMATION: hFLT2-11

<400> SEQUENCE: 40

Asn Ile Thr Val Thr Leu Lys Lys Phe Pro Leu
1               5                   10

<210> SEQ ID NO 41
<211> LENGTH: 9
<212> TYPE: PRT
<213> ORGANISM: mammalian
<220> FEATURE:
<223> OTHER INFORMATION: hFLT2-9

<400> SEQUENCE: 41

Thr Val Thr Leu Lys Lys Phe Pro Leu
1               5

<210> SEQ ID NO 42
<211> LENGTH: 7
<212> TYPE: PRT
<213> ORGANISM: mammalian
<220> FEATURE:
<223> OTHER INFORMATION: hFLT2-7

<400> SEQUENCE: 42

Thr Leu Lys Lys Phe Pro Leu
1               5

<210> SEQ ID NO 43
<211> LENGTH: 5
<212> TYPE: PRT
<213> ORGANISM: mammalian
<220> FEATURE:
<223> OTHER INFORMATION: hFLT2-5

<400> SEQUENCE: 43

Lys Lys Phe Pro Leu
1               5

<210> SEQ ID NO 44
<211> LENGTH: 13
<212> TYPE: PRT
<213> ORGANISM: mammalian
<220> FEATURE:
<223> OTHER INFORMATION: mFLT2

```
<400> SEQUENCE: 44

Ser Pro Asn Val Thr Val Thr Leu Lys Lys Phe Pro Phe
1               5                  10

<210> SEQ ID NO 45
<211> LENGTH: 16
<212> TYPE: PRT
<213> ORGANISM: mammalian
<220> FEATURE:
<223> OTHER INFORMATION: hFLT3

<400> SEQUENCE: 45

Arg Pro Val Lys Leu Leu Arg Gly His Thr Leu Val Leu Asn Pro Thr
1               5                  10                  15

<210> SEQ ID NO 46
<211> LENGTH: 16
<212> TYPE: PRT
<213> ORGANISM: mammalian
<220> FEATURE:
<223> OTHER INFORMATION: mFLT3

<400> SEQUENCE: 46

Ser Pro Val Arg Leu Leu His Gly Gln Thr Leu Val Leu Asn Pro Thr
1               5                  10                  15

<210> SEQ ID NO 47
<211> LENGTH: 13
<212> TYPE: PRT
<213> ORGANISM: mammalian
<220> FEATURE:
<223> OTHER INFORMATION: h/mFLK1

<400> SEQUENCE: 47

Ser Pro Phe Ile Ala Ser Val Ser Asp Gln His Pro Ile
1               5                  10

<210> SEQ ID NO 48
<211> LENGTH: 14
<212> TYPE: PRT
<213> ORGANISM: mammalian
<220> FEATURE:
<223> OTHER INFORMATION: h/mFLK2

<400> SEQUENCE: 48

Ile Pro Asn Leu Asn Val Ser Leu Pro Ala Arg Tyr Pro Glu
1               5                  10

<210> SEQ ID NO 49
<211> LENGTH: 19
<212> TYPE: PRT
<213> ORGANISM: mammalian
<220> FEATURE:
<223> OTHER INFORMATION: hFLK3

<400> SEQUENCE: 49

Ser Pro Ser His Gly Ile Glu Leu Ser Val Gly Glu Lys Leu Val Leu
1               5                  10                  15

Asn Pro Thr

<210> SEQ ID NO 50
<211> LENGTH: 19
<212> TYPE: PRT
<213> ORGANISM: mammalian
<220> FEATURE:
<223> OTHER INFORMATION: mFLK3
```

```
<400> SEQUENCE: 50

Ser Pro Pro His Glu Ile Glu Leu Ser Ala Gly Glu Lys Leu Val Leu
  1               5                  10                  15

Asn Pro Thr
```